United States Patent
West

(10) Patent No.: US 10,926,085 B1
(45) Date of Patent: *Feb. 23, 2021

(54) SYSTEM, METHOD AND APPARATUS FOR PLACING THERAPEUTIC DEVICES IN A HEART

(71) Applicant: MWest, LLC, Albuquerque, NM (US)

(72) Inventor: Michael B. West, Albuquerque, NM (US)

(73) Assignee: MWest, LLC, Albuquerque, NM (US)

( * ) Notice: Subject to any disclaimer, the term of this patent is extended or adjusted under 35 U.S.C. 154(b) by 96 days.

This patent is subject to a terminal disclaimer.

(21) Appl. No.: 16/175,659

(22) Filed: Oct. 30, 2018

Related U.S. Application Data

(63) Continuation of application No. 14/715,355, filed on May 18, 2015, now Pat. No. 10,111,768, which is a continuation of application No. 13/038,334, filed on Mar. 1, 2011, now Pat. No. 9,033,996.

(60) Provisional application No. 61/309,285, filed on Mar. 1, 2010.

(51) Int. Cl.
| | | |
|---|---|---|
| *A61M 25/00* | (2006.01) | |
| *A61M 25/06* | (2006.01) | |
| *A61B 17/00* | (2006.01) | |
| *A61N 1/05* | (2006.01) | |

(52) U.S. Cl.
CPC ......... *A61N 1/056* (2013.01); *A61M 25/0041* (2013.01); *A61M 25/0054* (2013.01); *A61M 25/0662* (2013.01); *A61B 2017/00243* (2013.01); *A61B 2017/00946* (2013.01); *A61M 2025/0081* (2013.01); *A61M 2210/125* (2013.01); *A61N 1/057* (2013.01); *A61N 2001/0585* (2013.01)

(58) Field of Classification Search
CPC .. A61N 1/05; A61N 2001/0585; A61N 1/059; A61N 2001/0578; A61B 18/1492; A61B 17/3468; A61F 2/966; A61M 25/0662; A61M 2025/0681
See application file for complete search history.

(56) References Cited

U.S. PATENT DOCUMENTS

| | | | |
|---|---|---|---|
| 4,863,442 A | | 9/1989 | DeMello et al. |
| 4,935,017 A | | 6/1990 | Sylvanowicz et al. |
| 5,120,323 A | | 6/1992 | Shockey et al. |
| 5,171,232 A | | 12/1992 | Castillo et al. |
| 5,322,064 A | * | 6/1994 | Lundquist .......... A61B 18/1492 600/381 |
| 5,488,960 A | | 2/1996 | Toner |
| 5,545,149 A | | 8/1996 | Brin et al. |
| 5,921,952 A | | 7/1999 | Desmond, III et al. |
| 6,061,588 A | | 5/2000 | Thornton et al. |
| 6,190,353 B1 | | 2/2001 | Makower et al. |
| 6,277,107 B1 | | 8/2001 | Lurie et al. |
| 6,408,214 B1 | | 6/2002 | Williams et al. |
| 6,638,268 B2 | | 10/2003 | Niazi |
| 6,714,823 B1 | | 3/2004 | De Lurgio et al. |
| 6,755,812 B2 | | 6/2004 | Peterson et al. |
| 6,802,840 B2 | | 10/2004 | Chin et al. |
| 6,979,290 B2 | | 12/2005 | Mourlas et al. |
| 7,041,097 B1 | | 5/2006 | Webler |

(Continued)

*Primary Examiner* — Katrina M Stransky
(74) *Attorney, Agent, or Firm* — Peacock Law P.C.; Janeen Vilven

(57) ABSTRACT

A system and method for positioning sheaths into the Coronary Sinus using a guiderail catheter.

15 Claims, 7 Drawing Sheets

(56) References Cited

U.S. PATENT DOCUMENTS

| | | |
|---|---|---|
| 7,303,560 B2 | 12/2007 | Chin et al. |
| 7,384,422 B2 | 6/2008 | Worley et al. |
| 7,462,167 B2 | 12/2008 | Kratz et al. |
| 7,462,184 B2 | 12/2008 | Worley |
| 7,623,899 B2 | 11/2009 | Worley et al. |
| 7,674,245 B2 | 3/2010 | Tockman et al. |
| 7,722,604 B2 | 5/2010 | Brown, III et al. |
| 7,976,531 B2 | 7/2011 | Johnson |
| 7,981,152 B1 | 7/2011 | Webler et al. |
| 8,126,570 B2 | 2/2012 | Manning et al. |
| 9,033,996 B1 | 5/2015 | West |
| 10,111,768 B1 | 10/2018 | West |
| 2003/0023296 A1 | 1/2003 | Osypka |
| 2003/0144657 A1* | 7/2003 | Bowe ................ A61M 25/0026 606/41 |
| 2004/0019359 A1 | 1/2004 | Worley et al. |
| 2004/0147826 A1 | 7/2004 | Peterson |
| 2004/0215139 A1 | 10/2004 | Cohen |
| 2005/0010237 A1 | 1/2005 | Niazi |
| 2007/0043413 A1 | 2/2007 | Eversull et al. |
| 2007/0265693 A1 | 11/2007 | Paskar |
| 2009/0036768 A1* | 2/2009 | Seehusen ............... A61L 29/106 600/424 |
| 2009/0319015 A1 | 12/2009 | Horn-Wyffels |
| 2009/0326629 A1 | 12/2009 | Drake et al. |
| 2009/0326630 A1 | 12/2009 | Tobin et al. |
| 2009/0326631 A1 | 12/2009 | Drake et al. |

* cited by examiner

SYSTEM, METHOD AND APPARATUS FOR PLACING THERAPEUTIC DEVICES IN A HEART

CROSS-REFERENCE TO RELATED APPLICATIONS

This application is a continuation of U.S. patent application Ser. No. 14/715,355, entitled "System, Method and Apparatus for Placing Therapeutic Devices in a Heart" filed on May 18, 2015, and issued as U.S. Pat. No. 10,111,768 on Oct. 30, 2018, which is a Continuation-In-Part of U.S. patent application Ser. No. 13/038,334, entitled "System, Method and Apparatus for Placing Therapeutic Devices in a Heart", filed on Mar. 1, 2011, and issued as U.S. Pat. No. 9,033,996 on May 19, 2015, which claims priority to and the benefit of the filing of U.S. Provisional Patent Application No. 61/309,285, entitled "WEST SYSTEM AND METHOD", filed on Mar. 1, 2010, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

INTRODUCTION

Minimally invasive procedures have been implemented in a variety of medical settings, e.g., for vascular interventions, such as angioplasty, stenting, embolic protection, electrical heart stimulation, heart mapping and visualization, delivery of pacemakers, and the like. These procedures generally rely on accurately navigating and placing instruments within a patient's vasculature.

During such procedures, a target vessel or structure may be accessed using a guide wire advanced through the intervening vasculature into the target vessel, thereby providing a "railway" to the vessel. One or more instruments, e.g., catheters, sheaths, and the like, may be advanced over the guide wire or "rail" into a vessel, heart, artery, vein, and/or other body cavity or lumen. However precise positioning often remains elusive with current systems and apparatus for positioning. Further, the guidewire alone is not desirable for guiding placement of sheaths in some locations within the body.

In some cases, a sheath placed within a body cavity or lumen may then be used to deliver an agent, a therapy or an additional device, such as a pacemaker lead, stent catheter, another sheath, and/or other devices. Many medical procedures require the introduction of specialized medical devices into the human heart. For example, electrical leads, such as pacemaker leads, defibrillation leads or leads used for cardioversion, or specialized catheters are frequently placed at specific locations within the heart to perform specialized cardiac procedures. Many of these medical devices, such as pacemaker leads, are very pliant and flexible. This flexibility is necessary to prevent damage, particularly to the patient's vasculature, during the period of time those products are present in the patient. However, because of this flexibility, it is quite difficult to advance these devices through the patient's vasculature into the heart without the use of some temporary, removable stiffening element with the device. For example, one method of stiffening certain medical devices is to introduce a stylet into the lumen of the medical device.

The typical procedure for introducing these devices into the heart requires passage through the patient's vasculature. One early approach to introduction of devices into the vasculature was to surgically cut an opening into the patient's vasculature. However, there are several disadvantages to this procedure. To address these disadvantages, percutaneous methods have been developed to create openings in the vasculature. Once an opening is created, frequently by use of a hollow needle, a dilator is usually inserted into the vasculature, which gradually increases the size of the opening. The dilator has a tapered end, which spreads apart the tissue at the puncture sight as it is advanced through the vasculature. Often the dilator will contain a lumen through which other medical devices may also be inserted into the vasculature.

As an example, in a typical procedure for introduction of an electrode lead into the heart, a guidewire is first introduced through the vasculature into the appropriate chamber of the heart. With the guidewire in place, a catheter/introducer or dilator/introducer combination is then passed over the guidewire and directed into the patient's body. The wire and/or dilator is then removed from the introducer. The introducer then provides a platform from which the lead may be introduced into the heart, frequently with a stylet placed within the lumen of the lead to assist in stiffening the structure of the lead and also to permit precise placement of the device within the heart.

While specialized medical devices are utilized throughout the human body, many have been used in the heart, in general and specifically in the coronary sinus. The coronary sinus is the largest cardiac vein in the heart and serves as a venous conduit from smaller veins within the myocardium to the right atrium. A tissue fold or primitive valve called the Thebesian valve, often partially obstructs the coronary sinus ostium ("CS OS"). It is generally thought that from a teleological perspective this "valve" helps prevent blood from backflowing into the coronary sinus as it is being pumped out of the right atrium. The valve is often formed by webs or bands of tissue that in some cases significantly obstruct the opening of the CS into the right atrium. Multiple fenestrations sometimes quite small are also frequently present further imposing an anatomical barrier to retrograde access by catheters and/or sheaths advanced from the right atrium. Located within the right atrium, generally, above the coronary sinus is an oval depression called the fossa ovalis. Between the inferior vena cava and the coronary sinus ostium is the Eustachian ridge. The location of each of these elements may vary from patient to patient. The coronary sinus is often used for electrophysiological procedures in the heart, including both diagnostic and treatment procedures. The coronary sinus can also be used as a location for introducing pacemaker leads to control both the left and right sides of the heart. Gaining access to the ostium of the coronary sinus is often difficult and time consuming. This may increase patient risk and overall procedure time and expense. This is especially true due to the wide degree of anatomic variations seen from one patient to the next. The anatomical structures located near the coronary sinus within the right atrium are not easily recognizable with fluoroscopic imaging, adding to this difficulty.

Current procedures available for introduction of devices such as pacemaker leads, implantable defibrillator leads, specialized catheters or devices used for cardioversion into the coronary sinus are frequently time consuming and difficult. To address this problem for a particular type of diagnostic catheter, various researchers have devised precurved, coronary sinus catheters, which, because of their curvature, can be advanced through the patient's vasculature over guidewires directly into the coronary sinus, where it can be used for diagnostic and treatment procedures such as disclosed in U.S. Pat. No. 6,277,107. Fixed precurved sheaths and catheters are known in the cardiac field. One limitation of fixed shape catheters and introducers as described in U.S. Pat. No. 6,277,107 and other commercially available catheters and sheaths is an inherent inability for uniform application throughout the highly varied patient anatomies. This is especially true given the typical patient referred for such procedures who more commonly manifest abnormal anatomy from a myopathic process. Thus many different fixed sheath shapes and fixed distal curvatures have been developed. The inherent disadvantage is the frequent need during implantation to open and use many sheaths as often times the first sheath or introducer chosen is too short or long or does not have the appropriate curvature for the particular anatomy. These features of the sheath or introducer cannot be modified by a user. Anatomic limitations inherent with the typical patient for whom these devices are implanted make a fixed curve sheath or catheter limited to only a single type of anatomic variant.

While several preshaped or biased introducers have been proposed, the shapes provided are still difficult to manipulate successfully and quickly into the coronary sinus. It typically takes a considerable amount to time and physician skill to manipulate these fixed shape introducers successfully into the opening of the coronary sinus.

SUMMARY OF THE INVENTION

One embodiment of the present invention is a method of introducing pacing therapy within a heart of a subject. The method comprises one or more of the following steps of introducing into the heart of the subject percutaneously a sheath positioned in the high right atrium wherein a distal end of the sheath is in a vertical position wherein the sheath has an open proximal end in communication with an open distal end and wherein the sheath is shaped with a curve; customizing a guiderail catheter into a shape compatible with the subject's anatomy wherein the guiderail catheter comprises a biocompatible polymer coating covering braided or woven elements that provide for shapeability of the guiderail catheter into a J curve at the distal end and an about 1:1 torque of the guiderail catheter from a proximal handle of the guiderail catheter to a distal tip of the guiderail catheter, a radiopaque marker positioned at the distal end of the guiderail catheter and wherein the guiderail catheter is lumenless; introducing a guiderail catheter into the heart of the subject through the distal end of the sheath; imaging with a fluoroscope the position of the sheath and guiderail catheter within the heart; advancing the distal end of the guiderail catheter about 10-15 cm past the distal end of the sheath into the right atrium of the heart to a position along the wall of the septum while maintaining at least some portion of the J curve previously shaped into the guiderail catheter; applying counter clockwise torque as the catheter is withdrawn slowly while maintaining contact with interatrial septum until the distal end of the railway catheter enters into the coronary sinus; advancing the distal end of the guiderail catheter into the CS until the guiderail catheter meets resistance from the anatomy of the CS; advancing the sheath along the guiderail catheter while applying retrograde traction on the guiderail catheter to rail the sheath over the guiderail catheter to a position within the CS and maintaining an alignment of the contours of the guiderail catheter and the sheath; and withdrawing the guiderail catheter from the proximal end of the sheath to introduce pacing therapy. A fluoroscope is used to image the position of the sheath and catheter in the body wherein the fluoroscope is in an Anterior-Posterior position of the fluoroscope as the guiderail catheter enters the body. A fluoroscope for imaging of the position of the guiderail catheter in the heart is a Left Anterior Oblique 30 degrees position as the guiderail catheter is positioned in the right side of the heart. In another embodiment of the present invention when the guiderail catheter enters the CS, the distal end of the guiderail catheter appears to jump into the CS in the fluoroscopic image. In another embodiment, the curve of the sheath is fixed. In a further embodiment, the curve of the sheath is a relaxed J curve.

In yet another embodiment a guiderail catheter for use in positioning sheaths into the Coronary Sinus comprises one or more of the following: a biocompatible polymer coating covering woven or braided elements that provide for shapeability of the guiderail catheter into a J curve at the distal end, a 1:1 torque of the guiderail catheter from a proximal handle of the guiderail catheter to a distal tip of the guiderail catheter, a radiopaque marker at the distal tip and wherein the guiderail catheter has been shaped to form a J curve at its distal tip. The guiderail may comprise one or more radiopaque markers. In another embodiment the guiderail catheter does not contain an opening at the distal tip. The catheter may contain a lumen or it may be lumenless. Further, a guiderail catheter may have a secondary shapeable tip that is secondary to the J curve at the distal end.

In yet another embodiment an assembly for use in lead therapy placement to the Coronary Sinus comprises a sheath of about 55 cm having a fixed preformed curve, an open distal end in communication with an open proximal end; and a guiderail catheter comprising a biocompatible polymer coating covering braided or woven elements that provide for shapeability of the guiderail catheter into a J curve at the distal end and an about 1:1 torque of the guiderail catheter from a proximal handle of the guiderail catheter to a distal tip of the guiderail catheter, a radiopaque marker positioned at the distal tip of the guiderail catheter and wherein the guiderail catheter is lumenless.

One embodiment of the present invention promises a guiderail catheter for use in positioning sheaths into the Coronary Sinus ("CS") comprising a biocompatible polymer coating covering woven or braided elements that provide for shapeability of the guiderail catheter into a J curve at the distal end, a 1:1 torque of the guiderail catheter from a proximal handle of the guiderail catheter to a distal tip of the guiderail catheter, a radiopaque marker at the distal tip and wherein the guiderail catheter has been shaped to form a J curve at its distal end and wherein the radiopaque marker at the distal tip does not receive nor transmit an electrical signal when the guiderail catheter is in use.

Another embodiment comprises an assembly for use in lead therapy placement to a Coronary Sinus and/or stent placement to the Coronary Sinus comprising a sheath of about 55 cm having a fixed preformed curve, an open distal end in communication with an open proximal end; and a guiderail catheter comprising a biocompatible polymer coating covering braided or woven elements that provide for shapeability of the guiderail catheter into a J curve at the distal end and an about 1:1 torque of the guiderail catheter from a proximal handle of the guiderail catheter to a distal tip of the guiderail catheter, and a radiopaque marker positioned at the distal tip of the guiderail catheter and wherein the radiopaque marker at the distal tip does not receive nor transmit an electrical signal when the guiderail catheter is in use. In one embodiment the stent is a flow restricting CS stent for treatment of chronic stable angina.

The radiopaque marker according to the above embodiments may comprise three or more radiopaque markers and or a plurality. The plurality of radiopaque markers may be spaced apart by a defined distance such that when the guiderail catheter is positioned in a heart of a subject in an orthogonal projection the plurality of radiopaque markers are presented in an en fosse presentation to a septum of the subject. The radiopaque marker is not connected to a wire for transmitting or receiving a current. Further the guiderail catheter is without a lumen or may contain a lumen. The guiderail catheter can have a shapeable distal tip that is secondary to the J curve at the distal end. The diameter may be about 2 mm.

It is an aspect of an embodiment of the present invention to provide a catheter based pacing therapy delivery system and assembly.

It is another aspect of one embodiment of the present invention to provide a guide catheter that is shapeable into a J curve at its distal tip which shape is maintained within about +/−1-10% or about +/−10-20% or about +/−20-30% of the original chord of the arc as initially shaped by the user when the guide catheter is in use as a guiderail as described herein.

Another aspect of this invention is to disclose a shaped introducer to be used for the introduction of medical devices into the coronary sinus by ordinarily skilled physicians without specific experience with the introducer. The shaped introducer may be a fixed shape or a non-fixed shape.

One aspect of one embodiment of the present invention provides a shapeable device, which assists in the efficient placement of medical devices, particularly small, flexible medical devices, such as electrode leads, into the coronary sinus, even by physicians without a high level of experience in using the device.

It is a further aspect of one embodiment of the present invention to provide a railway catheter for use by ordinarily skilled physicians without specific experience with the railway catheter to allow a medical device, such as a sheath for placement of flexible lead for use with a pacemaker, defibrillator or for cardioversion, to be introduced into the coronary sinus.

One aspect of an embodiment of the present invention provides for a method to gain CS access with a guiding catheter following which a sheath is placed over the guide catheter into the CS proper for use, for example, in facilitating deployment of LV epicardial leads by way of the CS in a more efficient manner.

One aspect of one embodiment of the present invention is a guiderail catheter which is applicable in most patients including those with dilated cardiomyopathy, pulmonary hypertension, cardiac chamber enlargement and various congenital structural anomalies as well as those with normal hearts.

Yet another aspect of one embodiment of the present invention provides for a method to facilitate more rapid (and often repeatable) CS access for Left Ventricular (LV) lead deployment.

One aspect of one embodiment of the present invention provides for a method for a single catheter to be used for CS access and for target vein selection. Many patients have branch veins that extend in unusual ways from the parent CS. The shapeable tip allows the same catheter, used to gain CS access, to be utilized for target branch vein selection.

Another aspect of one embodiment of the present invention provides for a guiderail catheter with a lumen for providing the ability to inject contrast and for guide wire placement to further facilitate final device placement.

Additional objects, aspects and advantages of embodiments of the present invention will be apparent in the following detailed description read in conjunction with the accompanying drawing figures.

One embodiment of the present invention overcomes the limitations discussed above for fixed curve sheaths or catheters by allowing the implanter to modify the catheter at the time of implant, to a shape that conforms or adapts to a particular anatomy of a patient. This flexibility in shaping of the guiderail catheter leads to cost and time savings and makes the overall risk of the procedure less by limiting repeated exchanges. Shapeability of the guiderail catheter by the implanter allows the implanter to modify and customize the catheter to match the specific patient needs and adapt the contour and configuration of the catheter accordingly. The introducers as disclosed in U.S. Pat. No. 6,277,107 are fixed in their shape, not capable of having a user introduce an increased or decreased curve into the sheath when dictated by the anatomy of the subject into which the sheath is to be placed and/or further does not have 1:1 torque and/or does not include braided or woven stiffening elements covered by a pliable biocompatible polymer coating.

DETAILED DESCRIPTION OF THE INVENTION

As used herein "a" or "the" means one or more unless otherwise indicated.

As used herein "about" means+/−0.1-10% variation.

As used herein "elastic deformation" means change in the shape or size of an object due to an applied force, which change is in-part or in-whole reversible.

As used herein "expended elasticity" means the change in shape that is beyond the elastic deformation.

One embodiment of the present invention provides for use of a lumen less catheter as a railway for sheath placement within the heart.

In another embodiment, a railway may exhibit one or more of the following properties or any combination thereof: push ability, kink resistance, malleable shape, softness, atraumatic distal end, one or more radiopaque markers, 1:1 torque and a proximal handle which may be ergonomically designed a railway with an internal lumen of the railway catheter. The features may be desirable to promote or facilitate the railway's navigation into a body lumen or cavity and subsequent placement of a sheath surrounding the railway into the same location. Yet further, it may be desirable to maintain the stability of placement of the sheath within a body cavity or lumen while removing the railway from its previous position.

Braid reinforcement used to impart characteristics of push ability, kink resistance, torque ability and the like are useful in one embodiment of the catheter. Although shapeable the construction of the catheter allows it to remain soft enough as to not pose a higher risk of damage during the implant. The catheter is not stiff or rigid but is constructed in such a way as to balance softness with shapability. The smooth contour of the catheter with contoured and rounded tip allow it to maneuver through the Thebesian valve atraumatically but yet its size provides adequate body to allow it to function as a rail for the sheath. The balance between enough stiffness to allow shaping and softness to minimize risk of injury are unique features of this catheter.

Figure 1:
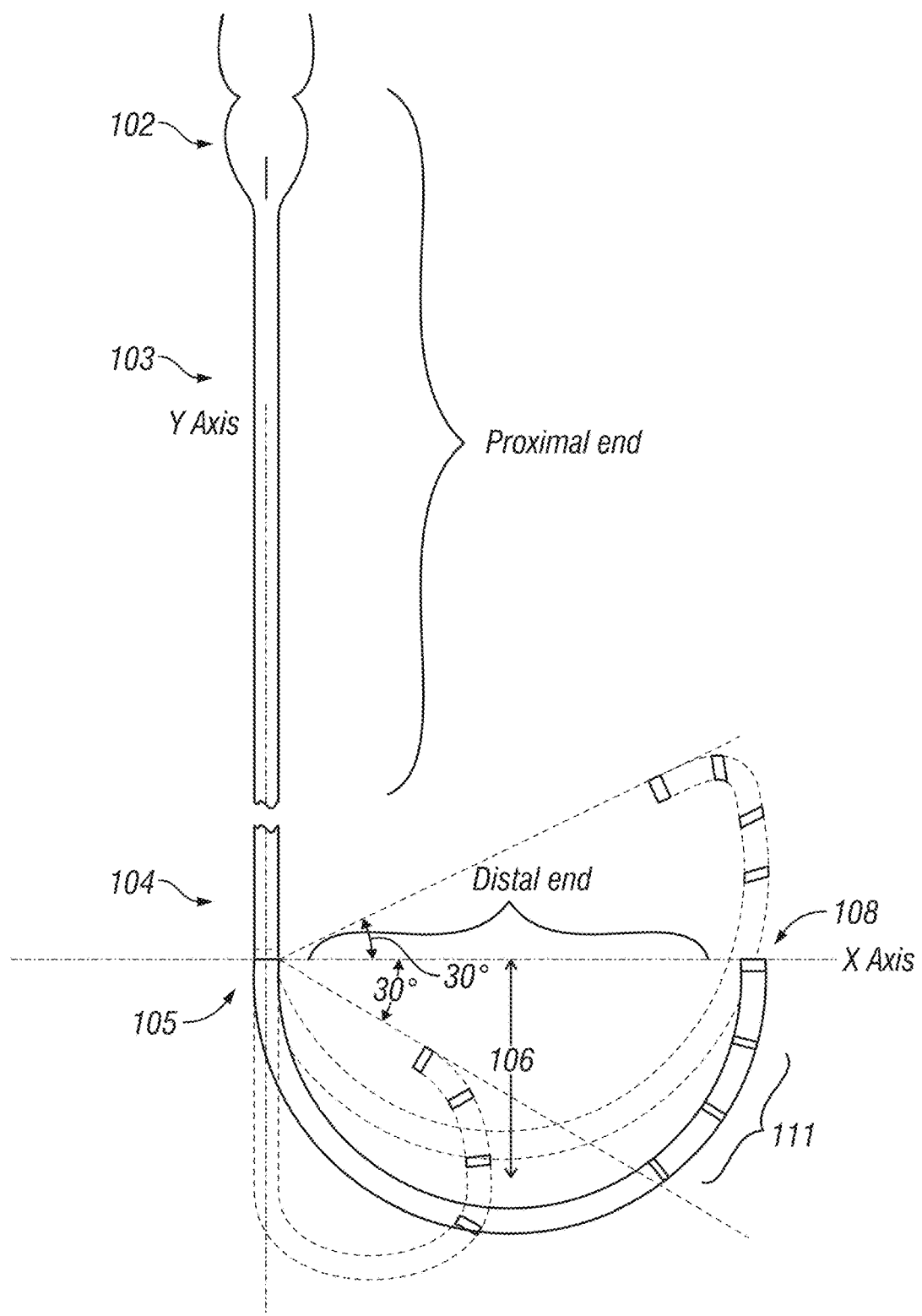
FIG. 1 illustrates a guiderail catheter (also referred to herein as a railway catheter) that can be shaped by manual stripping to exhibit different curves as its distal end.

Referring now to FIG. 1, a railway catheter (sometimes referred to herein as guide catheter or catheter) is illustrated according to one embodiment of the present invention. A handle 102 of the device provides an ergonomic design to facilitate advancing, withdrawal and rotation of the catheter. There is a raised "flange" (not shown) at the distal end of the handle to correspond with the curve at the distal end of the catheter. A straight elongated proximal portion of the guide catheter 103 extends from the handle and may project for about 60 cm. The "transition zone" of the catheter is that portion where the straight segment meets the initial curvature of the arc. This site of the catheter is illustrated as 104 and 105. At or near this site along the most distal portion of the elongated and straight segment the catheter may be "shaped" to result in a greater chord of the arc. This provides a greater degree of "reach" for CS placement of the catheter in larger hearts with dilated right atria. This feature highlights the customizable nature of the catheter allowing a single catheter to be use in virtually all patients. The ability to fashion a "real time" shape into the catheter allows the implanter to adjust the contour of the guide catheter to facilitate CS access adjusting and individualizing the shape for any given patient. Having achieved CS access with the current guide catheter a delivery sheath may then be "railed" or advanced over the catheter and placed into the CS. The actual shape of the sheath chosen for placement into the CS then becomes less important for CS access and may then be chosen to focus on selective target vein cannulation and lead delivery. The measurement of the chord length of the arc is depicted by a line drawn from 105 to 108 in FIG. 1. After final shaping of the catheter the chord should approximate 10-12 cm in length for use in a human heart of average size and shape. With the elongated straight segment of the catheter as the abscissa or y-axis the distal end or tip of the catheter would lie between 30 degrees above or below the x-axis. More than one "pass" may be necessary and the catheter may need to taken out and reshaped with more or less curve to the distal end of the catheter or shaping along the length of the catheter to adapt it to fit the patient's anatomy/RA size. The manufactured curve on the guide catheter is roughly equal to that seen with the Elmhurst curve, for example. This places the tip of the catheter at roughly 30 degrees below the x-axis as shown in the illustration.

After shaping or "stripping" the distal portion of the catheter (described later), the tip would lie at about 30 degrees above the x axis. The segment height or sagitta is represented by 106. From the horizontal x-axis, the vertical distance from the center or keystone of the arc to the x-axis is about 5-7.5 cm. It is important to note that these are general measurements and not meant to indicate absolutes. The shapeable nature of the catheter allows more or less curve to be placed that may ultimately be needed to accommodate individual variations in anatomy as illustrated. Final shaping is performed with these measurements in mind but are not limiting. The tip of the distal end of the catheter in FIG. 1 108 is rounded and smooth. It may be radiopaque as are the other two or more pairs of markers 204. The tip is rounded and made flush with the sides of the catheter. This rounded tip reduces the risk of traumatic dissection while the catheter is being advanced within the heart and vasculature. Further, this rounded as opposed to "squared off" or "blunted" catheter tip allows for more easy passage of the catheter through the fenestrations and other obstructions variably present at the OS of the CS. One or more pairs of radiopaque markers are aligned in such a way as to provide appropriate alignment of the catheter toward the septum and for improved depth perception during two-dimensional fluoroscopic imaging. An imager such as a fluoroscope may be utilized but is not limited thereto as other imagers known to one of ordinary skill in the art may be utilized with the appropriate image intensifier.

Figure 2A:
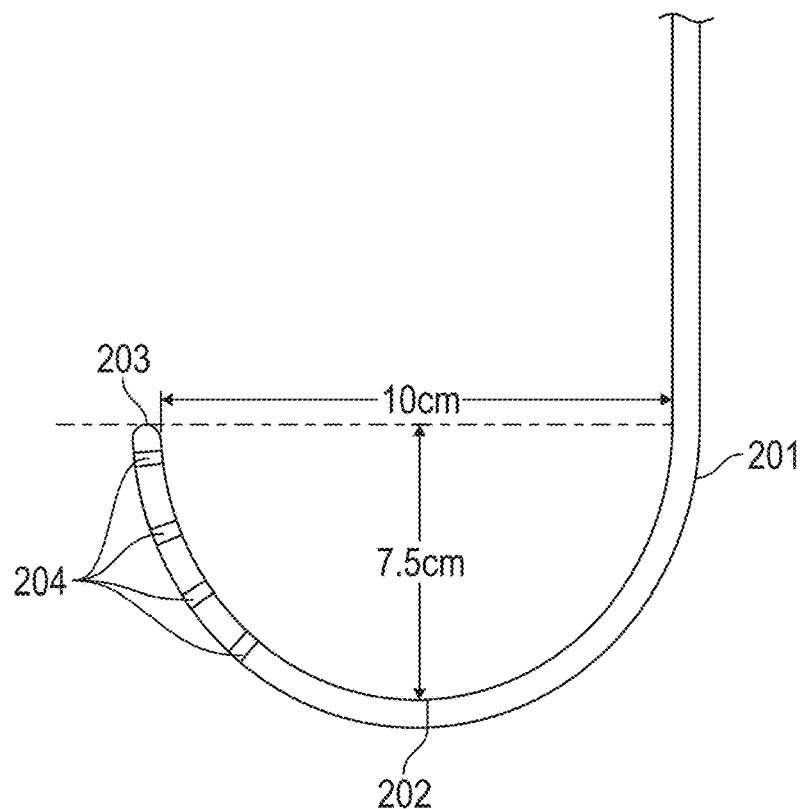
FIG. 2a illustrates a device railway catheter comprising a shaped curve at its distal tip.
Figure 2B:
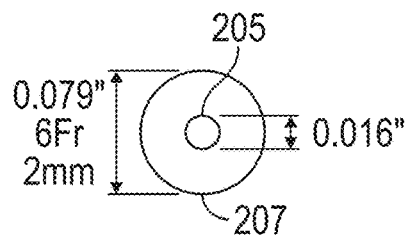
FIG. 2b illustrates a cross section of one embodiment of the device with an internal lumen.
Figure 2C:
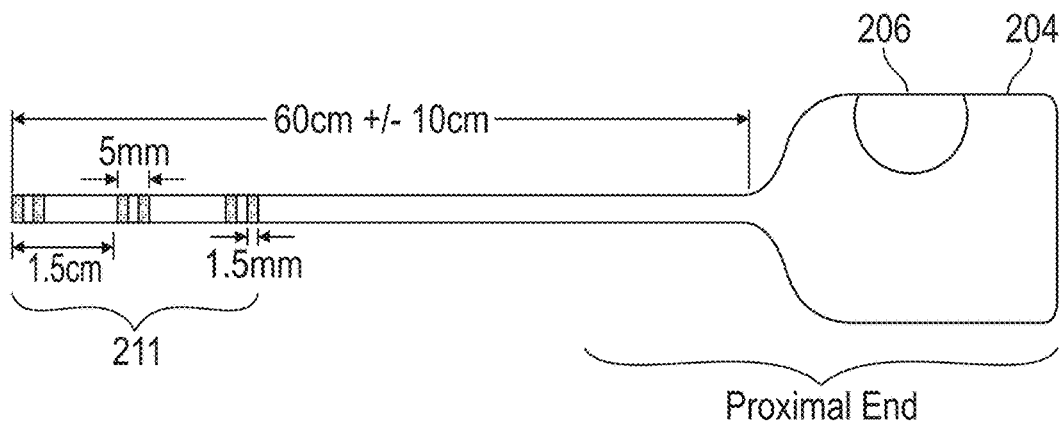
FIG. 2c illustrates the device extended and straight having extended its elasticity.

Referring now to FIG. 2C, a guiderail catheter according to one embodiment of the present invention is illustrated. A handle 204 of the guide catheter may be shaped to facilitate improved maneuverability. Different handles of different shapes and sizes to accomplish an ergonomic design are within the scope of this invention. The handle itself is about 4.5 cm in length. It may be about 2 cm wide and may narrow at the mid portion to about 1.5 cm to aide ergonomics. The body of the handle may be about 3 cm and the distal portion about 1.5 cm. The distal portion of the handle tapers to blend into the straight elongated portion of the catheter. A small flange 206 is aligned with the manufactured curvature of the catheter. This flange is meant to provide the implanter with the ability to monitor catheter position while watching the catheter movement during fluoroscopy. The distal tip of the catheter 209 is further illustrated in FIG. 2B which represents an "end on" view of a catheter. A guiderail catheter may include an internal lumen 205 in one embodiment of the catheter, and an outer edge 207 of the catheter. A catheter as illustrated is about 2 mm in diameter.

The lumen 205 is large enough at about 0.016 mm to receive an about 0.014 mm guide wire. Use of a guide wire would allow for enhanced advancement of the guiderail catheter and for sub selection of target veins after CS access is achieved. The current illustration with the lumen is also intended to add a greater degree of shapeability (secondary) to the distal portion 204 of the catheter so that the CS access guiderail catheter itself could be used to sub select a target vein with a more obtuse takeoff from the parent CS.

One embodiment of the present invention provides for a guide catheter of about 65 cm in length and about 2 mm in diameter. Catheters of different diameter and different lengths are within the scope of this invention. For example a catheter of between about 25 cm-55 cm is suitable. A catheter of between about 55 cm-85 cm is also suitable. Alternatively a catheter of greater than 85 cm is suitable for larger subjects. A subject may be a human or other animal such as a horse or a dog. The guiderail catheter as described allows adequate extension of the catheter out of the distal end of the sheath. For example about 12 to 15 cm length of the guiderail catheter beyond the distal end of the sheath is usually adequate to allow it to be placed into the CS avoiding diversion of the guiderail catheter by the shape of the sheath. Longer guide catheters are sometimes associated with less responsiveness and a torque ratio of greater than one. If a longer sheath is needed for a larger subject or for an inferior as opposed to a superior approach then the construction of the catheter is altered to maintain the desirable responsiveness of one to one torque. Alterations in typically applied manufacturing processes are utilized to achieve this.

One embodiment of a guide catheter comprises a woven or braided element embedded in the wall of the catheter. It may be covered by an extruded polymer to provide resistance to flexibility of the catheter in the absence of applied force. For example the catheter is comprised of double braided or woven interior elements and the external surface of the catheter is covered in a biocompatible material. The element may be composed of bendable wire or other stiffening material which may be shaped. Additionally, the center core of the catheter may contain malleable filaments to enhance the implanter's ability to create a user dependent secondary curve toward the distal end of the guiderail catheter.

Another embodiment of the guide catheter comprises a tip that is atraumatic and/or rounded and/or radiopaque or any combination thereof. There may be one or more radiopaque markers in the catheter. For example the one or more radiopaque markers may comprise radiopaque marker sets that are positioned along the guiderail catheter in pairs with each pair comprising a first radiopaque marker and a second radiopaque marker forming a first pair set having a defined distance between the first radiopaque marker and the second radiopaque marker of the first pair set. A second pair comprising a first radiopaque marker and a second radiopaque marker having a defined distance there between. The first pair set being separated from the second pair set by a defined distance. A subsequent pair set may have the same or different spacing between the first radiopaque marker and the second radiopaque marker of the subsequent pair set as compared to the first pair set and/or the second pair set. The subsequent pair set may be separated from the second pair set by a defined distance which may be the same or different distance as compared to the distance between the first pair set and the second pair set. For example, when there are three markers, the markers may be spaced about 15 mm one from another. However other spacing are suitable as will be apparent to one of ordinary skill in the art. Radiopaque markers are utilized according to one method of one embodiment of the present invention to align and position the catheter in the correct position of the subject prior to the terminal manipulation for CS access using an imaging device such as a fluoroscope. The spacing of the markers enhances the two and three-dimensional perspective. Small, closely paired markers separated by greater distances along the distal end of the catheter enhance the ability to distinguish the perpendicular alignment of the catheter toward the septum as opposed to a more anterior or posterior position. This ability to align the catheter in the appropriate position facilitates CS cannulation as described in one or more embodiments.

The relatively short length and braided polymer construction of the catheter allow for "one to one" torque from the catheter handle to the catheter tip to facilitate manipulation of the catheter tip from outside the body. In a preferred embodiment the braiding is double braiding.

In another embodiment, a guiderail catheter contains a handle at the proximal end of the guide catheter. When present the handle may be shaped in such a way as to improve the tactile "feel" of catheter manipulation. In another embodiment, there is also a small marker (raised flange) on the handle to indicate handle alignment with the curvature of the catheter.

Another embodiment of the present invention provides for a guide catheter with an opening at the proximal end and the distal end and a lumen connecting the openings which lumen is suitable for accepting a guide wire for example an about 0.014 mm guide wire. The guide wire is positioned into the catheter at the proximal opening and through the lumen to extend past the distal end of the guide catheter through the distal opening. The lumen adds to the shapeability of the catheter without resulting in unwanted stiffness or rigidity or flexibility.

Another embodiment provides for a guide catheter comprising multi-braided construction and a polymer jacket covering the exterior such as that found in the Bard Viking CS catheter (catalogue no. 40099 as of Mar. 1. 2010). The exterior is a material that is biocompatible, for example PVC, PTFE, PES, PE, PU, PEI, PC, PEEK, PS, PP or any combination thereof or other suitable biocompatible polymer types, but not limited thereto, as other polymer types which are well known in the art are also suitable. The current embodiment contains small gauge pacing and recording wires within a core of the guide catheter to enhance the catheter's ability to be shaped. In alternative embodiment the guide catheter does not contain pacing or recording wires and/or the radiopaque markers are not in communication with pacing or recording wires and/or the radiopaque markers are not competent or capable to receive or transmit an electrical stimulus because the radiopaque markers are not part of an electrical circuit and/or communication circuit and are not connected to components that are designed to transmit a current and/or a signal from and/or to the tissue. In shaping the guiderail catheter the elastic deformation is used to the operator's advantage. The shaping of the guiderail catheter will be shaped to the point of expended elasticity. Wherein the new shape introduced into the guiderail catheter by the user is substantially maintained after shaping. This shapeability allows the shaper to adjust the length of reach of the terminal curvature of the arc which is illustrated in FIG. 1b.

Shaping the guiderail catheter to adjust the chord of the arc, the catheter may then be altered to accommodate hearts of various sizes, shapes and orientations within the chest. This allows a single catheter to be utilized for most all hearts referred for an LV pacing lead.

Another embodiment of the present invention provides for a guiderail catheter with a guide tip at the distal portion beginning at 202 and that is more shapeable in the same or different plane from the chord of the guiderail catheter arc (see FIG. 1, 107). This additional shapeability allows the same guiderail catheter to gain entry into the main CS and then to sub-select a target branch vein through which a guide wire is advanced. This is done with a single catheter used for both CS access and target vein selection. Utilizing a single catheter to access the CS, rail the sheath, place a guide wire into the target vein and then sub select the target vein help reduce cost, time and risk to the patient. With a guidewire in the target vein the sheath is then able to be advanced into the target vein to allow direct placement of the pacing lead and or stent into the target branch vein.

Several of the embodiments of the present invention are directed generally to an assembly comprising a railway catheter also known as guiderail catheter and a sheath apparatus which may be used with one or more of the methods for delivering instruments and/or agents during a medical procedure and assemblies for medical procedures as described herein. More particularly, several embodiments of the present invention are directed to guiding sheaths for accessing body lumens and/or delivering instruments into body lumens of a patient, and to an assembly and apparatus for achieving the same.

Briefly, various embodiments disclosed herein provide for an assembly comprising railway catheter and sheath having certain properties, such as push ability and/or, kink resistance, while preserving ease of removal of the railway catheter from the sheath once the railway catheter has allowed the sheath to be positioned easily in the desired body lumen.

Figure 3:
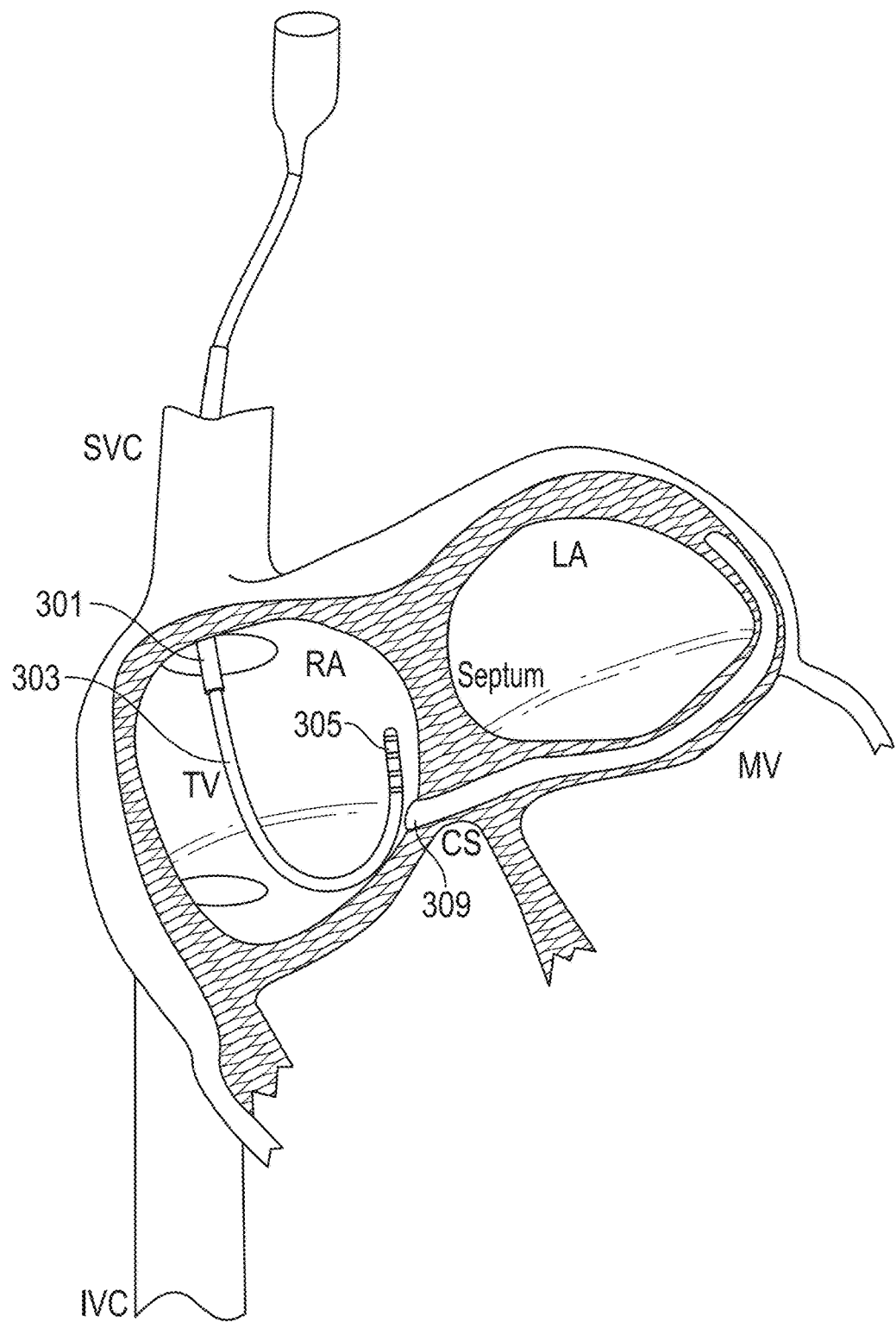
FIG. 3. illustrates a railway catheter and sheath assembly positioned within the heart.
Figure 4:
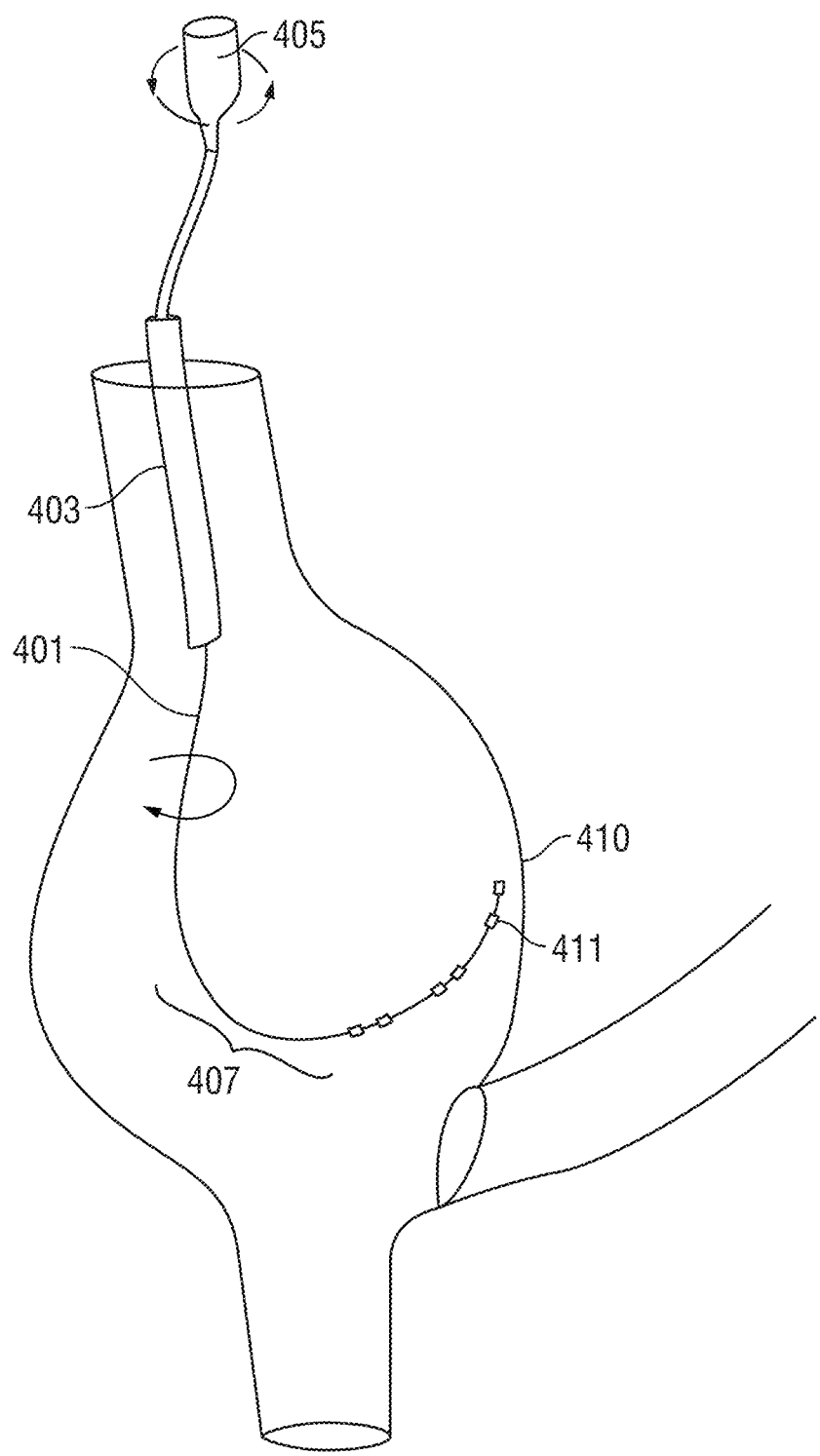
FIG. 4. illustrates a device positioned within the heart.
Figure 5:
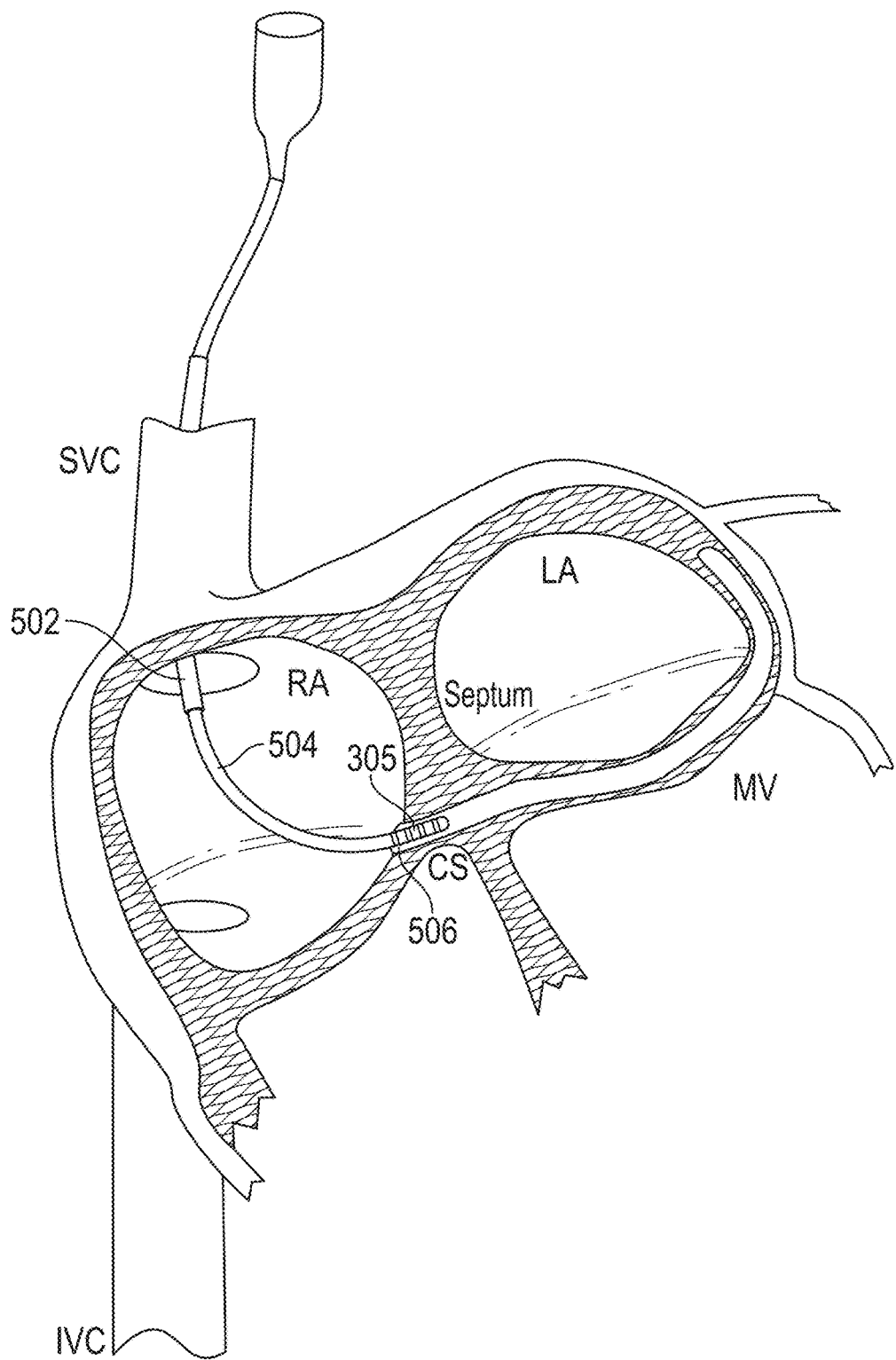
FIG. 5 illustrates the railway catheter positioned within the heart.

Referring now to FIGS. 3, 4 and 5, steps of catheter placement in the CS OS comprises positioning and rotational movements according to one embodiment of the method described herein. Referring now to FIG. 3, a catheter as described according to one embodiment of the present invention is positioned in the heart. After central access from above the sheath 301 is positioned near the junction of the superior vena cava (SVC) and the right atrium (RA). The sheaths used for this purpose may have varying lengths and curvatures, one suitable sheath is for example the Medtronic MB2. Placing the sheath at the junction of the superior vena cava and the right atrium minimizes the impact the shape of the sheath may have on positioning and/or trajectory of the guiderail catheter as it is introduced to the heart through the sheath. Positioning in this manner minimizes any deflection by the sheath upon the natural course taken by the guiderail catheter. The fluoroscope is positioned in the anterior-posterior (AP) position until the guiderail catheter is advanced to near the tip of the sheath. When the guiderail catheter reaches the distal end of the sheath, both now located near the SVC/RA junction, the fluoroscope is moved to the left anterior oblique (LAO) at about 30° position. The distal end of the guiderail catheter is monitored while slowly advancing the guiderail catheter toward the septum. The radiopaque markers on the distal end of the guiderail catheter help with proper placement of the guiderail catheter. The movement of the guiderail catheter in the about 30° LAO configuration will be from superior to inferior, from lateral to septal and on the imaging screen, will be from left to right. In this way, the general movement of the catheter will often allow the catheter to be deflected up along the interatrial septum 305. This placement is especially desirable in patients who have a partial obstruction of their CS from Thebesian valve tissue that prevents a direct or inferior entry into the CS. Most obstructions of the CS OS involve tissue covering the lower (inferior) portion of the OS. Placing the guiderail catheter in the position illustrated in FIG. 3 with manipulation of the catheter as described herein will allow the catheter to slowly slide down between the septum and any valve tissue obstructing the OS. The circular or curvilinear positioning of the guiderail catheter within the RA as depicted in FIG. 3 prior to final CS approach is illustrated.

Referring now to FIG. 4, a method of placement of the guiderail catheter is illustrated according to one embodiment of the present invention. The guiderail catheter 401 is slowly withdrawn while simultaneously rotating the catheter 401 counterclockwise 407. Counter clockwise torque 407 is applied to the guiderail catheter 401 while slowly pulling it back through the sheath 403. Care is taken not to over rotate the catheter 401 keeping the distal end of the guiderail catheter in contact with the interatrial septum. Slowly and steadily withdrawing the guiderail catheter 401 while simultaneously applying counterclockwise torque 407 will most often be associated with movement leftward. Most often the guiderail catheter 401 will promptly advance or "jump" forward into the CS 409 at that time. This is most often seen on fluoroscopy as sudden although sometimes subtle movement of the guiderail catheter distal tip 410 toward the left heart or left to right on the fluoroscopic image.

Referring now to FIG. 5, after the guiderail catheter 504 is seen to advance into the CS it is placed out the CS as far as it will go without resistance. Care is taken not to advance the guiderail catheter beyond the point where the guiderail catheter moves freely. CS access has now been achieved and the next step is to advance or "rail" the sheath 502 over the guiderail catheter into the CS. It is important that the guiderail catheter be carefully advanced 508 but more important that the guiderail catheter be in contour with the direction the sheath will take as it is advanced over the guiderail catheter. Avoid pushing the guiderail too far distally such that it begins to buckle proximally (within the RA) from any distal obstruction to prevent complete dislodgement of the delivery system. It should be noted that as the sheath is "railed" over the guiderail catheter the shape of the guiderail catheter will transiently change to accommodate the lumen of the sheath.

After the guiderail catheter 504 is well positioned in the CS and the slack, if any, is removed then the sheath 502 is ready to be advanced. It is important that the guiderail catheter be held in one hand while the other hand is used to gently slide the sheath over the guiderail catheter. Again it is important that the guiderail catheter and sheath contours be aligned with one another and that each follows a direct and gentle path into the CS. Avoid buckling and/or "backup" of the delivery system. Often the sheath will get "caught up" at the CS OS 506 because of the tissue from the Thebesian valve. This can be overcome in a number of ways. The easiest thing to do at this point is to "press" the sheath forward while applying retrograde traction on the guiderail catheter. If resistance is still encountered and the sheath stays "hung up" at the OS, then the sheath itself is gently rotated in both directions (clockwise and counterclockwise) while still applying forward pressure on the sheath. This will often allow the "lip" of the sheath to pass through valve tissue on out into the CS. It is important to remember to continue to stabilize the guiderail catheter while advancing the sheath, applying retrograde traction as needed to keep the guiderail from advancing to the point of buckling or backing out of the CS completely. After the sheath is positioned in the CS, a relaxed and gentle contour to the sheath is maintained. The guiderail catheter is then removed and the sheath flushed. A small amount of intravenous contrast dye is then injected to confirm the position.

Figure 6:
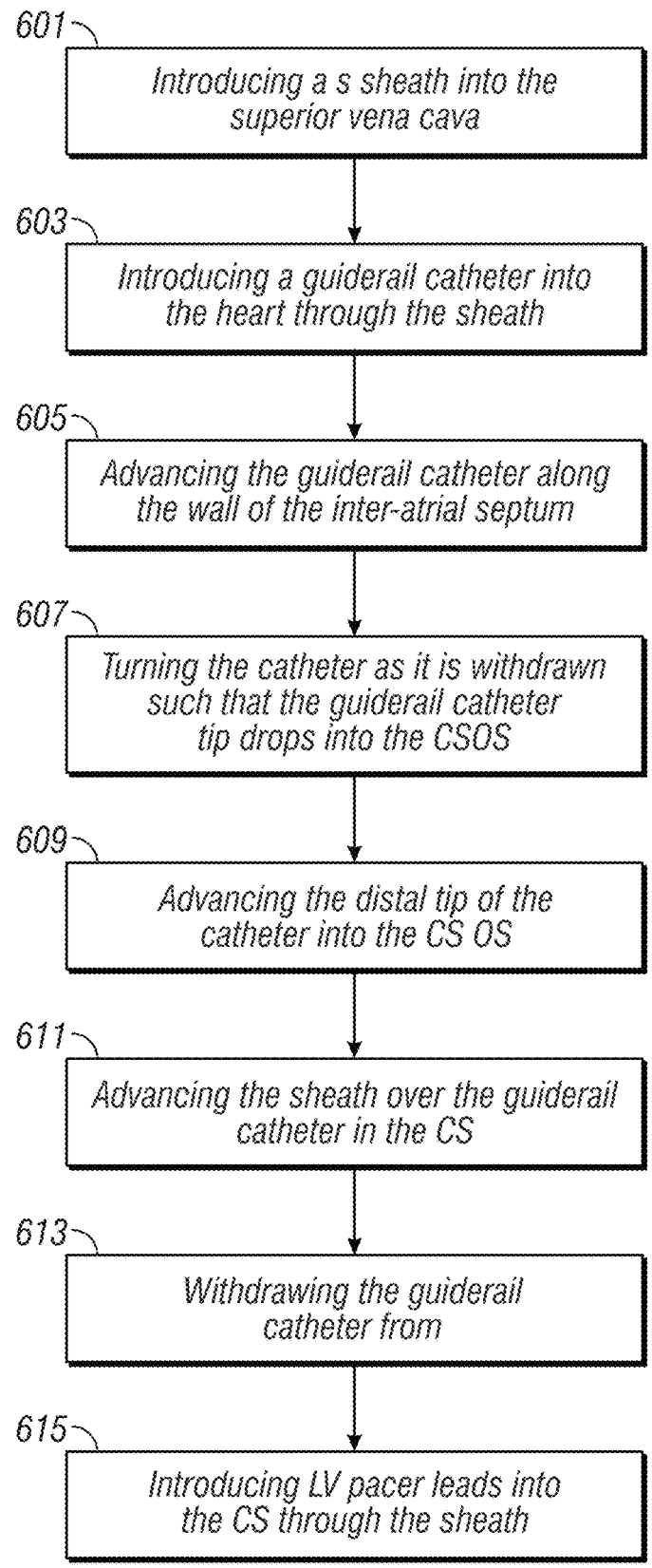
FIG. 6 illustrates a method of LV placement according to one embodiment of the present invention.
Figure 7:
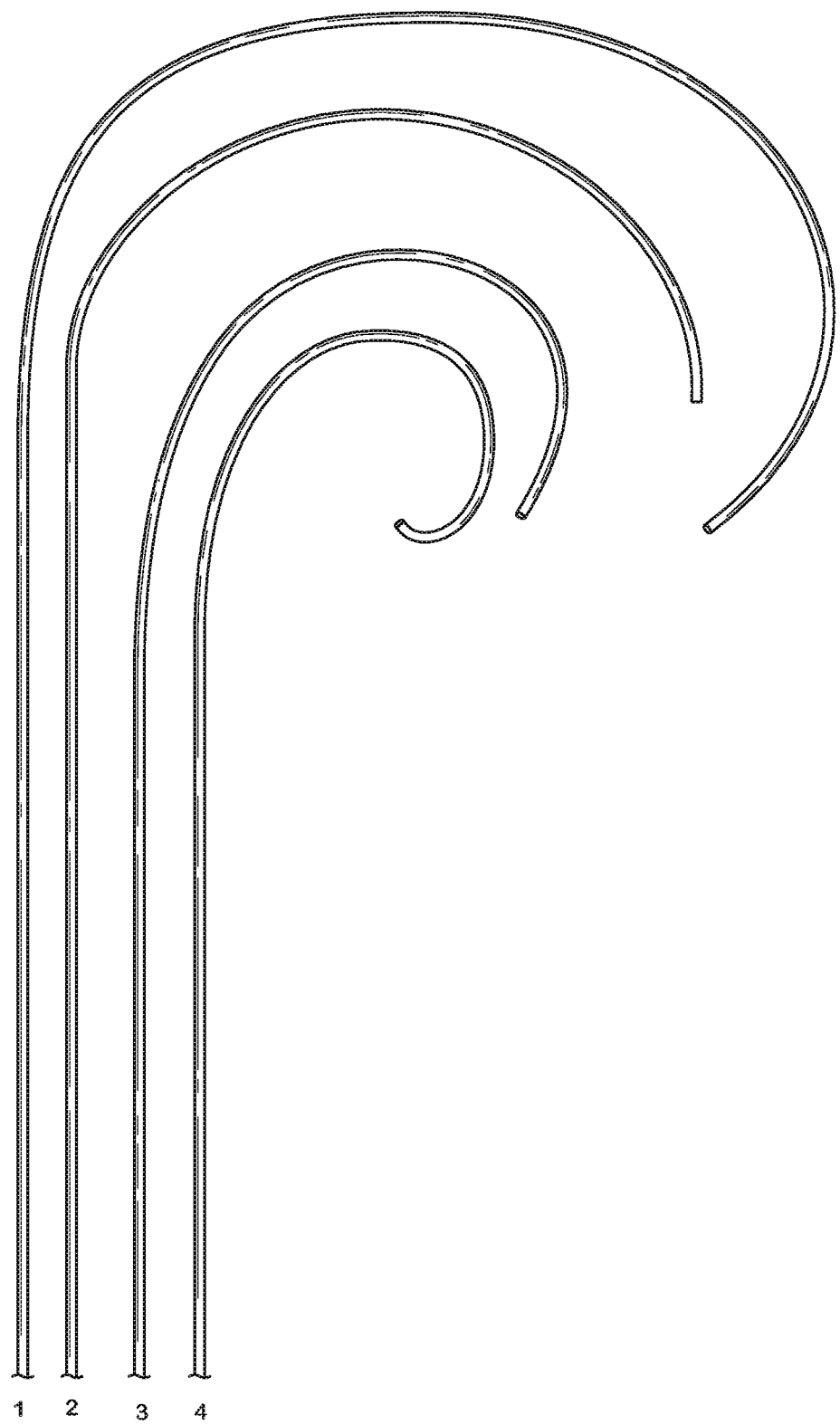
FIG. 7 illustrates different curves of the distal end of the guiderail catheter that are induced by manual stripping.

Referring now to FIG. 6, a method for LV lead placement is described according to one embodiment of the present invention. Introduction of the sheath percutaneously into the superior vena cava 601 is followed by introduction of the guiderail catheter into the sheath and heart 603. The guiderail catheter is advanced into the heart 605 to a position against the septum as illustrated in FIG. 3. The catheter is maneuvered to the OS of the CS by withdrawing the guiderail catheter through the proximal end of the sheath while rotating the guiderail catheter to position the tip toward the OS 607. The sheath is advanced over the guiderail catheter once the guiderail catheter is in place in the CS 611. The guiderail catheter is withdrawn from the proximal end of the sheath 613. The LV leads are positioned in the heart through the sheath for delivery of the designated therapy 615.

The indications for LV lead placement and cardiac resynchronization therapy (CRT) are rapidly expanding. Many physicians have difficulty accessing the CS leading to increased cost to the patient and increased patient risk. Furthermore, the described process can be repeated multiple times utilizing the same equipment over again which enhances the cost effectiveness of the invention.

The ability to easily access the CS and to do this reproducibly in patients requiring LV lead placement is an asset for clinically effective CRT.

Embodiments of the assembly, apparatus and method have been shown to allow access to CS of patients in reduced time, for example less than one minute in the vast majority of cases. Even if an apparatus of the assembly dislodges completely from the desired location the process can easily be repeated with the same equipment providing cost and time savings.

The following is a discussion of non-limiting examples of several of the embodiments of the present invention as disclosed herein.

Many sheaths of varying size and shape are available for use through which LV leads are deployed through the CS onto the epicardial surface of the LV. A good sheath for most patients is one with a gentle curve and of intermediate length (45-50 cm). The MDT MB2™ is one such sheath but other sheaths are suitable as well.

One purpose of accessing the CS with the guiderail catheter is to position the sheath within the CS through which a LV pacing lead is ultimately delivered into a target branch vein. The usual approach is superior from the subclavian vein, typically the left. Using Seldinger technique the central vein is accessed through which a sheath is positioned with the tip of the sheath at the junction of the SVC and Right Atrium (RA). At this point, the sheath dilator and guide wire are removed. The sheath is flushed. The guiderail catheter is then readied for insertion. The distal about 15-20 cm of the guiderail catheter matching the extent of the guiderail catheter that will initially extend beyond the sheath, is then shaped by carefully "stripping" that portion into a curvilinear configuration helping it to form and substantially maintain the shape as illustrated in FIG. 1. In a preferred embodiment stripping is accomplished manually.

Another point of difficulty for successful lead deployment is the valve of Vieuessens. This valve is the anatomic divide of the CS and the Great Cardiac Vein (GCV). Most often this valve is easily traversed. There are occasions however when the valve acts to obstruct the placement of either the guiderail catheter or the sheath far enough out to place an LV lead. To overcome this obstruction a Wholly™ wire is employed. This wire has a straight floppy tip with a radiopaque marker. After the wire is manipulated through the valve of Vieuessens a dilator, for example from the MDT Attain Select II™, is used to slide over the wire into the distal CS (and GCV). Using the same "rail" technique the sheath is advanced over the straight dilator into the distal CS and position confirmed by injecting intravenous contrast material.

The radiopaque markers should be laid out in full and not overlapped on the fluoro image to ensure correct positioning of the guiderail catheter. This is generally referred to an "en fosse" or "full face" fluoroscopic presentation. Sometimes, as in the case of a markedly dilated RA, the catheter needs more "reach" in order for the tip of the guiderail catheter to engage the CS OS. To accomplish this, simply remove the catheter and shape the catheter higher up on the shaft or the elongated straight segment. Typically a gloved and moistened hand using the base of the second finger against the thumb. The motion required to impart the correct "shape" on the guiderail catheter is with a striping-like action to shape the distal portion of the catheter. By performing this same "stripping" action more proximal on the catheter the chord portion of the arc of the curve is extended.

Because of various degrees of distorted anatomy from cardiomyopathic hearts there is often some resistance to simply advancing the sheath over the guiderail catheter placed in the CS. This can be overcome by slowly advancing the sheath forward while applying some retrograde traction on the CS catheter. In the case of a fenestrated Thebesian valve the sheath abuts against the outer tissue of the narrow fenestration and there is resistance. Forward pressure applied to the sheath on and then off while retrograde traction is applied to the guiderail catheter being careful not to pull the guiderail catheter back will advance the sheath into the CS.

In a preferred embodiment the CS guiderail catheter is maintained out into the CS when advancing the sheath. The sheath will advance over the guiderail catheter as a "rail". After the sheath is positioned, the catheter is removed and the sheath is flushed. A small amount of contrast dye is used to validate appropriate positioning the distal portion of the CS. Dissection of the CS occurs easily and is best avoided even though this complication rarely results in serious problems. It can delay or prevent a lead from being placed during the procedure. Finding the true lumen of the CS after a dissection is sometimes quite difficult.

One or more features of embodiments of the present invention include the ability to shape the distal portion of the catheter to compliment the recipient heart as not all hearts are alike. Orientations of the heart in the chests of large and/or obese patients are often quite varied from the orientation of the heart in small individuals. Likewise, different disease processes account for many and varied hurdles for LV lead placement including but not limited to chamber enlargement, elevated pressures, valve regurgitation and anatomic variations in the CS anatomy. Some of these variations include the Thebesian valve, the valve of Vieuessens and target vein takeoff variations (tangential vs. oblique). Additionally, variable vein size, tortuosity, and most importantly, anatomic location relative to the "ideal" LV epicardial pacing sight. Appropriate position for LV lead deployment is between the 1 and 4 o'clock position in the LAO view of the mitral annulus. Conversely, in the right anterior oblique (RAO) projection the ideal sight is at the junction of proximal and middle thirds of the LV. Embodiments of the present invention provide to the implanter the ability to access the coronary sinus and great cardiac vein quickly and easily so that a pacing lead or other therapy or device may be properly positioned and lead to improvement in the patient's clinical heart failure status and/or outcome.

Several of the embodiments of the present invention affords the implanting physician a single tool with suitable flexibility to apply real time modifications to individual patients. One might analogize one embodiment of the guiderail catheter to a crescent wrench. Instead of a large tool box filled with various fixed end wrenches, the implanter reaches for a single tool with enough flexibility to get the job done with less cost, time and risk The present invention has been described in terms of preferred embodiments, however, it will be appreciated that various modifications and improvements may be made to the described embodiments without departing from the scope of the invention. The entire disclosures of all references, applications, patents, and publications cited above and/or in the attachments, and of the corresponding application(s), are hereby incorporated by reference.

What is claimed is:

1. A guiderail catheter for use in positioning sheaths into a heart comprising:
a biocompatible polymer coating covering woven or braided elements that provide for shapeability into a curve of the guiderail catheter with manual stripping at a distal end, shapeability of the guiderail catheter with manual stripping at a distal tip that is secondary to the curve at the distal end, a 1:1 torque of the guiderail catheter from a proximal handle of the guiderail catheter to the distal tip of the guiderail catheter, a radiopaque marker at the distal tip and wherein the guiderail catheter has been shaped to form a curve at its distal end and wherein the radiopaque marker at the distal tip does not receive nor transmit an electrical signal when the guiderail catheter is in use and wherein there are no pacing or recording wires in the guiderail catheter and wherein the radiopaque marker comprises a first radiopaque marker pair with each marker of the first radiopaque marker pair separated by a first distance and a second radiopaque marker pair with each marker of the second radiopaque marker pair separated by a second distance wherein the first radiopaque marker pair is separated from the second radiopaque marker pair by a third distance which is greater than the first distance and the second distance such that the radiopaque marker enhances a two and three dimensional perspective of the guiderail catheter when the guiderail catheter is in use.

2. The guiderail catheter of claim 1 further comprising three or more pairs of radiopaque markers.

3. The guiderail catheter of claim 1 wherein the guiderail catheter is without a lumen.

4. The guiderail catheter of claim 1 wherein the guiderail catheter contains a lumen.

5. The guiderail catheter of claim 1 has a diameter wherein the diameter is about 2 mm.

6. The guiderail catheter of claim 1 wherein the third distance that separates the first radiopaque marker pair and the second radiopaque marker pair is such that when the guiderail catheter is positioned in the heart of a subject in an orthogonal projection the first radiopaque marker pair and the second radiopaque marker pair are presented in an en fosse presentation to a septum of the subject.

7. The guiderail catheter of claim 1 wherein the first radiopaque marker pair and the second radiopaque marker pair are not connected to a wire for transmitting or receiving a current.

8. An assembly for use in lead therapy placement to a heart comprising:
a sheath having a fixed preformed curve, an open distal end in communication with an open proximal end; and
a guiderail catheter comprising a biocompatible polymer coating covering braided or woven elements that provide for shapeability of the guiderail catheter at a distal end into a curve, an about 1:1 torque of the guiderail catheter from a proximal handle of the guiderail catheter to a distal tip of the guiderail catheter, and a radiopaque marker positioned at the distal tip of the guiderail catheter and wherein the radiopaque marker at the distal tip does not receive nor transmit an electrical signal when the guiderail catheter is in use and wherein there are no pacing or recording wires in the guiderail catheter and wherein the radiopaque marker comprises a first radiopaque marker pair with each marker of the first radiopaque marker pair separated by a first distance and a second radiopaque marker pair with each marker of the second radiopaque marker pair separated by a second distance wherein the first radiopaque marker pair is separated from the second radiopaque marker pair by a third distance which is greater than the first distance and the second distance such that the radiopaque marker enhances a two and three dimensional perspective of the guiderail catheter when the guiderail catheter is in use.

9. The assembly of claim 8 further comprising three or more pairs of radiopaque markers at the distal tip.

10. The assembly of claim 8 wherein the guiderail catheter contains a lumen.

11. The guiderail catheter of claim 8 wherein the first radiopaque marker pair and the second radiopaque marker pair are spaced apart by a defined distance such that when the guiderail catheter is positioned in the heart of a subject in an orthogonal projection the first radiopaque marker pair and the second radiopaque marker pair are presented in an en fosse presentation to a septum of the subject.

12. The assembly of claim 8 wherein the first radiopaque marker pair and the second radiopaque marker pair at the distal tip are not capable of receiving nor transmitting an electrical signal.

13. An assembly for use in therapeutic device placement in a heart comprising:
a sheath having a preformed curve, an open distal end in communication with an open proximal end; and
a guiderail catheter comprising a biocompatible polymer coating covering braided or woven elements that provide for shapeability of the guiderail catheter at a distal end into a curve, manual shapeability of a distal tip that is secondary to the curve at the distal end, an about 1:1 torque of the guiderail catheter from a proximal handle of the guiderail catheter to the distal tip of the guiderail catheter, and a radiopaque marker positioned at the distal tip of the guiderail catheter wherein the radiopaque marker at the distal tip does not receive nor transmit an electrical signal when the guiderail catheter is in use and wherein there are no pacing or recording wires in the guiderail catheter and wherein the radiopaque marker comprises a first radiopaque marker pair with each marker of the first radiopaque marker pair separated by a first distance and a second radiopaque marker pair with each marker of the second radiopaque marker pair separated by a second distance wherein the first radiopaque marker pair is separated from the second radiopaque marker pair by a third distance which is greater than the first distance and the second distance such that the radiopaque marker enhances a two and three dimensional perspective of the guiderail catheter when the guiderail catheter is in use.

14. The assembly according to claim 13 wherein the therapeutic device is a stent.

15. The assembly of claim 13 wherein the first radiopaque marker pair and the second radiopaque marker pair at the distal tip are not capable of receiving nor transmitting an electrical signal.

\* \* \* \* \*